US008513309B2

(12) United States Patent
Klein

(10) Patent No.: US 8,513,309 B2
(45) Date of Patent: Aug. 20, 2013

(54) PERFLUOROCARBONS FOR USE IN TREATING PRURITUS

(75) Inventor: Gerald Klein, Morrisville, NC (US)

(73) Assignee: Oxygen Biotherapeutics, Inc., Morrisville, NC (US)

(*) Notice: Subject to any disclaimer, the term of this patent is extended or adjusted under 35 U.S.C. 154(b) by 138 days.

(21) Appl. No.: 13/250,682

(22) Filed: Sep. 30, 2011

(65) Prior Publication Data
US 2012/0083510 A1   Apr. 5, 2012

Related U.S. Application Data

(60) Provisional application No. 61/389,089, filed on Oct. 1, 2010, provisional application No. 61/393,687, filed on Oct. 15, 2010.

(51) Int. Cl.
  A61K 31/13    (2006.01)
  A61K 31/445   (2006.01)
  A61K 31/02    (2006.01)
  A61K 31/025   (2006.01)

(52) U.S. Cl.
  USPC .......... 514/672; 514/317; 514/743; 514/747; 514/757; 514/759; 514/761

(58) Field of Classification Search
  USPC .................. 514/672, 317, 743, 747, 757, 759, 514/761
  See application file for complete search history.

(56) References Cited

U.S. PATENT DOCUMENTS

| 3,911,138 | A | 10/1975 | Clark, Jr. |
|---|---|---|---|
| 3,977,988 | A | 8/1976 | Tokiwa et al. |
| 3,996,141 | A | 12/1976 | Updike |
| 4,173,654 | A | 11/1979 | Scherer |
| 4,289,499 | A | 9/1981 | Clark et al. |
| 4,411,872 | A | 10/1983 | Bramson |
| 4,452,818 | A | 6/1984 | Haidt |
| 4,453,028 | A | 6/1984 | Lagow |
| 4,686,024 | A | 8/1987 | Scherer, Jr. et al. |
| 4,879,062 | A | 11/1989 | Moore |
| RE33,451 | E | 11/1990 | Clark, Jr. |
| 5,045,296 | A | 9/1991 | Pfeffer et al. |
| 5,158,536 | A | 10/1992 | Sekins et al. |
| 5,295,953 | A | 3/1994 | Richard et al. |
| 5,300,528 | A | 4/1994 | Graybill et al. |
| 5,399,334 | A | 3/1995 | Kawakami et al. |
| 5,437,272 | A | 8/1995 | Fuhrman |
| 5,490,498 | A | 2/1996 | Faithfull |
| 5,674,913 | A | 10/1997 | Clark, Jr. |
| 5,824,703 | A | 10/1998 | Clark, Jr. |
| 5,840,767 | A | 11/1998 | Clark, Jr. |
| 6,167,887 | B1 | 1/2001 | Clark et al. |
| 6,251,371 | B1 | 6/2001 | Holmes et al. |
| 6,346,228 | B1 | 2/2002 | Choudhary et al. |
| 6,815,186 | B2 | 11/2004 | Clark, Jr. |
| 7,300,649 | B2 | 11/2007 | Tanojo et al. |
| 7,682,822 | B2 | 3/2010 | Noll et al. |
| 7,767,232 | B2 | 8/2010 | Nudler et al. |
| 2002/0068072 | A1 | 6/2002 | De Lacharriere et al. |
| 2005/0276865 | A1 | 12/2005 | Buyuktimkin et al. |
| 2005/0281890 | A1 | 12/2005 | San |
| 2007/0098662 | A1 | 5/2007 | Blume et al. |
| 2007/0224169 | A1 | 9/2007 | Sliwa, Jr. et al. |
| 2008/0312270 | A1 | 12/2008 | Brown et al. |
| 2009/0017147 | A1 | 1/2009 | Litner et al. |
| 2009/0169630 | A1 | 7/2009 | Ward et al. |
| 2009/0202617 | A1 | 8/2009 | Ward et al. |
| 2010/0144597 | A1 | 6/2010 | Ward et al. |
| 2010/0144861 | A1 | 6/2010 | Huvard et al. |
| 2010/0178347 | A1 | 7/2010 | Bullock et al. |
| 2010/0267842 | A1 | 10/2010 | Kiral et al. |
| 2011/0086923 | A1 | 4/2011 | Thompson et al. |
| 2011/0229575 | A1 | 9/2011 | Clauson et al. |
| 2011/0230566 | A1 | 9/2011 | Tamargo et al. |

FOREIGN PATENT DOCUMENTS

| EP | 0091820 | 10/1983 |
|---|---|---|
| EP | 0521492 | 1/1993 |
| WO | WO 81/00002 A1 | 1/1981 |
| WO | WO/91/03267 | 3/1991 |
| WO | WO/92/19232 | 11/1992 |
| WO | WO/92/19300 | 11/1992 |
| WO | WO/2004/028677 | 4/2004 |
| WO | WO/2005/097208 | 10/2005 |

OTHER PUBLICATIONS

PCT International Search Report issued on Oct. 19, 1995 in connection with International Application No. PCT/US1995/05993.
PCT International Search Report issued on Apr. 1, 1997 in connection with International Application No. PCT/US1996/018801.
PCT International Search Report issued on Aug. 27, 1999 in connection with International Application No. PCT/US1998/24632.
PCT International Search Report issued on Oct. 17, 2007 in connection with International Application No. PCT/US2007/068910.
PCT International Preliminary Report on Patentability issued on Nov. 17, 2008 in connection with PCT International Application No. PCT/US2007/068910.
Written Opinion of the International Searching Authority issued on Oct. 17, 2007 in connection with International Application No. PCT/US2007/068910.
PCT International Search Report issued on Dec. 9, 2009 in connection with International Application No. PCT/US2009/05715.
Written Opinion of the International Searching Authority issued on Dec. 9, 2009 in connection with International Application No. PCT/US2009/05715.

(Continued)

*Primary Examiner* — Raymond Henley, III
(74) *Attorney, Agent, or Firm* — Gary J. Gershik; Cooper & Dunham LLP

(57) ABSTRACT

The subject application provides a method of treating pruritus comprising administering to the skin of a subject afflicted with pruritus an amount of a perfluorocarbon effective to treat the pruritus. The subject application also provides a method of alleviating a symptom of psoriasis comprising administering to the skin of a subject afflicted with psoriasis an amount of a perfluorocarbon effective to alleviate the symptom of psoriasis. The subject application also provides a perfluorocarbon composition for use in treating a subject afflicted with pruritus or psoriasis. The subject application further provides a pharmaceutical composition comprising an amount of a perfluorocarbon for use in treating pruritus or psoriasis.

20 Claims, 1 Drawing Sheet

(56) References Cited

OTHER PUBLICATIONS

PCT International Search Report issued on Feb. 12, 2010 in connection with International Application No. PCT/US2009/06159.

PCT International Preliminary Report on Patentability issued May 31, 2011 in connection with PCT International Application No. PCT/US2009/006159.

Written Opinion of the International Searching Authority issued on Feb. 12, 2010 in connection with International Application No. PCT/US2009/06159.

PCT International Search Report issued on May 5, 2011 in connection with International Application No. PCT/US2011/28980.

Written Opinion of the International Searching Authority issued on May 5, 2011 in connection with International Application No. PCT/US2011/28980.

PCT International Search Report issued on Sep. 16, 2010 in connection with International Application No. PCT/US2010/02106.

Bekyarova G. (1997) "Suppressive effects of FC-43 perfluorocarbon emulsion on enhanced oxidative haemolysis in the early postburn phase" Burns 23(2):117-121.

Clark L. et al. (1979) "A New Look at the Vapor Pressure Problem in Red Cell Substitutes" Int. Congr. Ser.-Ecerpta:486 (Proc. Int. Symp . . . ) 55-66.

Clark, Jr. et al. (1989) "Physiological Evaluation of Fluorocarbon Emulsions with Notes on F-Decalin and Pulmonary Inflation in the Rabbit" Mat. Res. Soc. Symp. Proc. :129-134.

Clark, L.C., Jr. et al. (1992) "Response of the Rabbit Lung as a Criterion of Safety . . . " Biomaterials, Artificial Cells and Immobilization 2-4:1085-1099.

Hoffman, R.E. et al. (1992) "Arterial Blood Gases and Brian Oxygen Availability Following Infusion of Intratracheal . . . " Biomaterials, Artificial Cells . . . 2-4:1073-1083.

Leach, C.L. et al. (1993) "Perfluorocarbon-associated gas exchange (partial liquid ventilation) . . . " Critical Care Medicine 21(9) 1270-1278.

Lin, Wen-Huey and Richard J. Lagow (1990) "The Synthesis of Highly Fluorinated Alkycyclohexanes for Use As Oxygen Carriers . . . " Journal of Fluorine Chemistry 50:345-358.

Moore, R. E. and Clark (1982) "Synthesis and Physical Properties of Perfluorocompounds Useful as Synthetic Blood Candidates" Oxygen Carrying Colloidal Blood Substitutes: 50-60.

Okamoto H. et al. (1984) "Fate of perfluorochemical impurities contained in both perfluorodecaline (FDC) and perfluorotripropyl" Chemical Abstracts (100) (3).

Schaefer (2009) "PFC for Oxygen Delivery to Skin" Cosmetic and Toiletries [online] Dec. 1, 2009.

Schurch, S. et al. (1976) "Direct determination of surface tension in the lung" Physiological Sciences (73) (12):4698-4702.

Shaffer, T.H. et al. (1994) "Perfluorochemical Liquid as a Respiratory Medium" Artif. Cells Blood Substit. Immobil. Biotechno. (22)2: 315-326.

Smith et al. (1997) "Partial Liquid Ventilation: a Comparison Using Conventional and High Frequency Techniques in an Animal Model . . . " Crit. Care Med. 25(7):1179-1185.

Tutuncu, A.S. et al. (1993) "Comparison Ventilatory Support with Intratracheal Perfluorocarbon Administration . . . " American Review of Respiratory Disease (148): 785-792.

Varushchenko, R.M. et al. (1996) "Thermodynamics of Vaorization of Some Cyclic Perfluorocarbons" Fluid Phase Equilibria, 126(1996) 93-104.

Weinkle (2010) "Efficacy and Tolerability of Admixing 0.3% Lidocaine with Dermicol-P35 27G for the Treatment of Nasolabial Folds" Dermatologic Surgery 36(3):316-320.

Written Opinion of the International Searching Authority issued on Sep. 16, 2010 in connection with International Application No. PCT/US2010/002106, filed Jul. 27, 2010.

International Preliminary Report on Patentability issued Jan. 31, 2012 in connection with PCT/US2010/002106, filed Jul. 27, 2010.

PCT International Search Report issued May 4, 2012 in connection with PCT/US2011/054273, filed Sep. 30, 2011.

Written Opinion of the International Searching Authority issued May 4, 2012 in connection with PCT/US2011/054273, filed Sep. 30, 2011.

Mar. 1, 2012 Office Action issued in connection with U.S. Appl. No. 12/590,996, filed Nov. 17, 2009.

Apr. 2, 2012 Amendment in Response to Mar. 1, 2012 Office Action issued in connection with U.S. Appl. No. 12/590,996, filed Nov. 17, 2009.

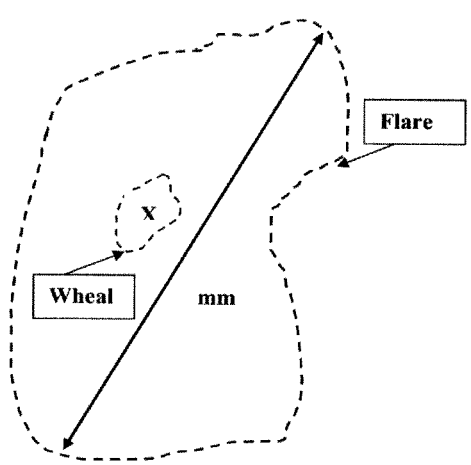

PERFLUOROCARBONS FOR USE IN TREATING PRURITUS

This application claims benefit of U.S. Provisional Application No. 61/389,089, filed Oct. 1, 2010 and U.S. Provisional Application No. 61/393,687, filed Oct. 15, 2010, the entire content of each of which is hereby incorporated by reference herein.

Throughout this application various publications, published patent applications, and patents are referenced. The disclosures of these documents in their entireties are hereby incorporated by reference into this application in order to more fully describe the state of the art to which this invention pertains.

BACKGROUND OF THE INVENTION

Pruritus

Pruritus (itching) is a sensation that a patient instinctively attempts to relieve by scratching or rubbing. It is a symptom and not a disease, and may accompany a primary skin disease or a systemic disease. (The Merck Manual, 1999.)

Skin diseases causing severe pruritus vary, and include scabies, pediculosis, insect bites, urticaria, atopic dermatitis, contact dermatitis, lichen planus, miliaria, and dermatitis herpetiformis. Dry skin often causes severe generalized pruritus. (The Merck Manual, 1999.)

Systemic conditions that cause generalized pruritus, usually without skin lesions, include obstructive biliary disease, uremia (frequently associated with hyperparathyroidism), lymphomas, leukemias, and polycythemia rubra vera. Pruritus may also occur during the later months of pregnancy. Many drugs (especially barbiturates and salicylates) can cause pruritus. Less well-defined associations with generalized pruritus include hyperthyroidism, diabetes mellitus, and internal cancers of many types. Pruritus is uncommonly purely psychogenic. (The Merck Manual, 1999.)

Persistent scratching may produce redness, linear urticarial papules, excoriation of preexisting papules, fissures, and elongated crusts along scratch lines, which may obscure the underlying disease. Lichenification and pigmentation may also result from prolonged scratching and rubbing. Occasionally, patients who complain of severe generalized pruritus have few signs of scratching or rubbing the skin. (The Merck Manual, 1999.)

Conventionally caine-based anesthetics are avoided, but lotions or creams containing 0.125% to 0.25% menthol can be useful. Ultraviolet B to the skin and oral cholestyramine can be helpful in uremia and cholestasis and at times in undiagnosed cases. Topical corticosteroids seldom alleviate generalized pruritus (without dermatitis) but may uncommonly be useful if used with lubricants in elderly patients with dry skin. (The Merck Manual, 1999.)

If a drug has been ruled out as the cause of pruritus, hydroxyzine (10 to 50 mg po q 4 h prn) can be prescribed or, for more severe cases, minimal and gradually increasing doses of trimeprazine or the antidepressant doxepin. If antihistamines are helpful, their sedative effect may be the reason. Antihistamines are more likely to cause intolerable side effects in the elderly. More recently several newer low-sedating antihistamines have become available, including astemizole, loratadine, and cetirizine. These drugs have been used with limited success in the treatment of pruritus. (The Merck Manual, 1999.)

Given the wide range of conditions which can cause pruritus, and the lack of a single effective therapy, additional therapies for pruritus are needed.

Dermatitis (Eczema)

Dermatitis is superficial skin inflammation, characterized histologically by epidermal edema and clinically by vesicles (when acute), poorly marginated redness, edema, oozing, crusting, scaling, usually pruritus, and lichenification caused by scratching or rubbing. (The Merck Manual, 1999.) As noted above, dermatitis (eczema) usually causes pruritus.

Authorities generally disagree about how to use the synonymous terms eczema and dermatitis. Often eczema refers to vesicular dermatitis, but some authorities restrict eczema to mean chronic dermatitis. Some also refer to dermatitis as spongiotic dermatitis because spongiosis (intraepidermal edema) is a histologic feature. (The Merck Manual, 1999.)

Dermatitis includes contact dermatitis and atopic dermatitis. Contact dermatitis is the acute or chronic inflammation, often asymmetric or oddly shaped, produced by substances contacting the skin and causing toxic (irritant) or allergic reactions. Atopic dermatitis is the chronic, pruritic, superficial inflammation of the skin, frequently associated with a personal or family history of allergic disorders (e.g., hay fever, asthma). (The Merck Manual, 1999.)

Psoriasis

Psoriasis is a common chronic, recurrent disease characterized by dry, well-circumscribed, silvery, scaling papules and plaques of various sizes. Psoriasis varies in severity from one to two lesions to widespread dermatosis, sometimes associated with disabling arthritis or exfoliation. The cause is unknown, but the thick scaling has traditionally been attributed to increased epidermal cell proliferation and concomitant dermal inflammation. The response of psoriasis to the immunosuppressive drug cyclosporine suggests that the primary pathogenetic factor may be immunologic. (The Merck Manual, 1999.) Psoriasis causes pruritus.

Conventionally, lubricants, keratolytics, topical corticosteroids, topical vitamin D derivatives and anthralin are tried first in patients with a limited number of lesions. Exposure to sunlight is also beneficial though occasionally sunburn may induce exacerbations. Systemic antimetabolites (e.g., methotrexate) are used only in patients with severe skin or joint involvement. Immunosuppressive drugs (e.g., cyclosporine, tacrolimus, mycophenolate mofetil) have been used in severe and recalcitrant cases, but these drugs are not currently approved in the U.S. for treatment of psoriasis. Systemic corticosteroids should not be used because side effects, including severe exacerbations or pustular lesions, may occur during treatment (even with increasing doses) or after treatment. (The Merck Manual, 1999.)

Perfluorocarbons

Perfluorocarbons (PFCs) are known to be chemically and biologically inert substances which are capable of dissolving very large volumes of gases, including oxygen and carbon dioxide, at concentrations much larger than water, saline and plasma. In addition, PFCs can transport these gases to diffuse across distances. Thus, PFCs can be a convenient and inexpensive means to deliver high levels of oxygen or other therapeutic gases to tissues and organ systems.

PFCs that are commonly used in medical research are non-toxic, biologically inert, biostatic liquids at room temperature with densities of about 1.5-2.0 g/ml and high solubilities for oxygen and carbon dioxide. Such PFCs have been found to be efficient carriers of gases, both as emulsions for intravenous use and as neat liquids for liquid ventilation applications.

SUMMARY OF THE INVENTION

The subject application provides a method of treating pruritus comprising administering to the skin of a subject afflicted with pruritus an amount of a perfluorocarbon effective to treat the pruritus.

The subject application also provides a method of alleviating a symptom of psoriasis comprising administering to the skin of a subject afflicted with psoriasis an amount of a perfluorocarbon effective to alleviate the symptom of psoriasis.

The subject application also provides a perfluorocarbon composition for use in treating a subject afflicted with pruritus or psoriasis.

The subject application further provides a pharmaceutical composition comprising an amount of a perfluorocarbon for use in treating pruritus or psoriasis.

BRIEF DESCRIPTION OF DRAWINGS

FIG. 1: The wheal (edema) and flare (erythema) reaction can manifest itself in an irregular shape as illustrated in FIG. 1. X represents the site of the prick and the dotted line represents the outline of the wheal and flare reaction. The longest diameter should be measured using a standardized ruler.

DETAILED DESCRIPTION OF THE INVENTION

Embodiments of the Invention

The subject application provides a method of treating pruritus comprising administering to the skin of a subject afflicted with pruritus an amount of a perfluorocarbon effective to treat the pruritus.

In one embodiment, the pruritus is induced by histamine. In another embodiment, the pruritus is induced by a burn, an infection or hemodialysis. In another embodiment, the pruritus is a symptom of an inflammatory skin condition, xerosis, an inset bite, a dermatological allergic response, allergic dermatitis, allergic contact dermatitis, photodermatitis, hand dermatitis, miliaria rubra, eczema, atopic dermatitis or contact dermatitis. In another embodiment, the pruritus is anal pruritus, uremic pruritus or aquagenic pruritus. In another embodiment, the inflammatory skin condition is allergic vulvovaginitis. In yet another embodiment, the inflammatory skin condition is psoriasis.

The subject application also provides a method of alleviating a symptom of psoriasis comprising administering to the skin of a subject afflicted with psoriasis an amount of a perfluorocarbon effective to alleviate the symptom of psoriasis. In one embodiment, the symptom is pruritus.

In one embodiment, the molecular formula of the perfluorocarbon consists 9-12 carbon atoms. In another embodiment, the molecular formula of the perfluorocarbon consists 10 carbon atoms.

In one embodiment, the perfluorocarbon is perfluoro(tert-butylcyclohexane) perfluoro-n-butylcyclohexane, perfluorodecalin, trimethyl perfluorodecalin, perfluoroisopropyldecalin, perfluoro-tripropylamine, perfluorotributylamine, perfluoro-methylcyclohexylpiperidine, perfluoro-octylbromide, perfluoro-decylbromide, perfluoro-dichlorooctane, perfluorohexane, dodecafluoropentane, or a mixture thereof. In another embodiment, the perfluorocarbon is perfluoro(tert-butylcyclohexane) or perfluoro-n-butylcyclohexane. In another embodiment, the perfluorocarbon is perfluorodecalin.

In one embodiment, the perfluorocarbon is administered periodically. In another embodiment, the perfluorocarbon is administered once a day. In another embodiment, the perfluorocarbon is administered twice a day.

In one embodiment, the perfluorocarbon is administered topically. In another embodiment, the perfluorocarbon is administered topically to the portion of the subject's skin afflicted with the pruritus or psoriasis.

In one embodiment, the perfluorocarbon is in a perfluorocarbon gel. In another embodiment, the perfluorocarbon is in a perfluorocarbon emulsion.

In one embodiment, the subject is afflicted with edema, erythema or erythematous lesion. In another embodiment, the administration of the perfluorocarbon reduces the edema. In another embodiment, the administration of the perfluorocarbon reduces the erythema. In yet another embodiment, the administration of the perfluorocarbon reduces the erythematous lesion.

In an embodiment, the administration of the perfluorocarbon reduces the subject's edema, erythema or erythematous lesion within 1 minute of the administration. In another embodiment, the administration of the perfluorocarbon reduces the subject's edema, erythema or erythematous lesion within 2 minute of the administration. In another embodiment, the administration of the perfluorocarbon reduces the subject's edema, erythema or erythematous lesion within 3 minute of the administration. In another embodiment, the administration of the perfluorocarbon reduces the subject's edema, erythema or erythematous lesion within 5 minute of the administration. In another embodiment, the administration of the perfluorocarbon reduces the subject's edema, erythema or erythematous lesion within 15 minute of the administration. In another embodiment, the administration of the perfluorocarbon reduces the subject's edema, erythema or erythematous lesion within 30 minute of the administration. In yet another embodiment, the reduction of the subject's edema, erythema or erythematous lesion is at least 10%, 20%, 25%, 30%, 50%, 70%, 80% or 90% as compared to the placebo.

In one embodiment, the administration of the perfluorocarbon reduces the subject's edema, erythema or erythematous lesion by more than 10% compared to the placebo. In another embodiment, the administration of the perfluorocarbon reduces the subject's edema, erythema or erythematous lesion by more than 20% compared to the placebo. In another embodiment, the administration of the perfluorocarbon reduces the subject's edema, erythema or erythematous lesion by more than 25% compared to the placebo. In another embodiment, the administration of the perfluorocarbon reduces the subject's edema, erythema or erythematous lesion by more than 30% compared to the placebo. In another embodiment, the administration of the perfluorocarbon reduces the subject's edema, erythema or erythematous lesion by more than 50% compared to the placebo. In another embodiment, the administration of the perfluorocarbon reduces the subject's edema, erythema or erythematous lesion by more than 70% compared to the placebo. In another embodiment, the administration of the perfluorocarbon reduces the subject's edema, erythema or erythematous lesion by more than 80% compared to the placebo. In another embodiment, the administration of the perfluorocarbon reduces the subject's edema, erythema or erythematous lesion by more than 90% compared to the placebo. In yet another embodiment, the reduction of the subject's edema, erythema or erythematous lesion occurs within 1, 2, 3, 5, 15, or 30 minutes of the application of the perfluorocarbon to the subject's skin.

In one embodiment, the administration of the perfluorocarbon reduces subject-perceived itching. In an embodiment, the subject-perceived itching is measured by Visual Analogue Scale (VAS) score.

In an embodiment, the administration of the perfluorocarbon reduces the subject-perceived itching within 1 minute of the administration. In another embodiment, the administration of the perfluorocarbon reduces subject-perceived itching within 2 minute of the administration. In another embodiment, the administration of the perfluorocarbon reduces subject-perceived itching within 3 minute of the administration. In another embodiment, the administration of the perfluorocarbon reduces subject-perceived itching within 5 minute of the administration. In another embodiment, the administration of the perfluorocarbon reduces subject-perceived itching within 15 minute of the administration. In another embodiment, the administration of the perfluorocarbon reduces subject-perceived itching within 30 minute of the administration. In another embodiment, the reduction of subject-perceived itching is at least 10%, 20%, 25%, 30%, 50%, 70%, 80% or 90% compared to the placebo. In yet another embodiment, the percent reduction is measured in Visual Analogue Scale (VAS) score.

In one embodiment, the administration of the perfluorocarbon reduces subject-perceived itching by more than 10% compared to the placebo. In another embodiment, the administration of the perfluorocarbon reduces subject-perceived itching by more than 20% compared to the placebo. In another embodiment, the administration of the perfluorocarbon reduces subject-perceived itching by more than 25% compared to the placebo. In another embodiment, the administration of the perfluorocarbon reduces subject-perceived itching by more than 30 compared to the placebo 9. In another embodiment, the administration of the perfluorocarbon reduces subject-perceived itching by more than 50% compared to the placebo. In another embodiment, the administration of the perfluorocarbon reduces subject-perceived itching by more than 70% compared to the placebo. In another embodiment, the administration of the perfluorocarbon reduces subject-perceived itching by more than 80% compared to the placebo. In another embodiment, the administration of the perfluorocarbon reduces subject-perceived itching by more than 90% compared to the placebo. In an embodiment, the subject-perceived itching is measured in Visual Analogue Scale (VAS) score. In another embodiment, the reduction of subject-perceived itching occurs within 1, 2, 3, 5, 15, or 30 minutes of the application of the perfluorocarbon to the subject's skin.

In one embodiment, the administration of the perfluorocarbon relieves the subject's pruritus for 1-6 hours. In another embodiment, the administration of the perfluorocarbon relieves the subject's pruritus for 2 hours or more. In another embodiment, the administration of the perfluorocarbon relieves the subject's pruritus for 3 hours or more. In yet another embodiment, the administration of the perfluorocarbon relieves the subject's pruritus for 4 hours or more.

In one another embodiment, the administration of the perfluorocarbon relieves the subject's pruritus within immediately upon administration to the subject. In another embodiment, the administration of the perfluorocarbon relieves the subject's pruritus within 1 minute of the administration. In another embodiment, the administration of the perfluorocarbon relieves the subject's pruritus within 2 minute of the administration. In another embodiment, the administration of the perfluorocarbon relieves the subject's pruritus within 3 minute of the administration. In another embodiment, the administration of the perfluorocarbon relieves the subject's pruritus within 5 minute of the administration. In another embodiment, the administration of the perfluorocarbon relieves the subject's pruritus within 15 minute of the administration. In another embodiment, the administration of the perfluorocarbon relieves the subject's pruritus within 30 minute of the administration.

In one embodiment, the subject is a mammal. In another embodiment, the subject is a dog, a cat or a horse. In yet another embodiment, the subject human.

The subject application also provides a perfluorocarbon composition for use in treating a subject afflicted with pruritus or psoriasis.

The subject application further provides a pharmaceutical composition comprising an amount of a perfluorocarbon for use in treating pruritus or psoriasis.

In one embodiment, the molecular formula of the perfluorocarbon consists 9-12 carbon atoms. In another embodiment, the molecular formula of the perfluorocarbon consists 10 carbon atoms.

In one embodiment, the perfluorocarbon is perfluoro(tert-butylcyclohexane) perfluoro-n-butylcyclohexane, perfluorodecalin, trimethyl perfluorodecalin, perfluoroisopropyldecalin, perfluoro-tripropylamine, perfluorotributylamine, perfluoro-methylcyclohexylpiperidine, perfluoro-octylbromide, perfluoro-decylbromide, perfluoro-dichlorooctane, perfluorohexane, dodecafluoropentane, or a mixture thereof. In another embodiment, the perfluorocarbon is perfluoro(tert-butylcyclohexane) or perfluoro-n-butylcyclohexane. In another embodiment, the perfluorocarbon is perfluorodecalin.

All combinations and sub-combinations of the various elements of the compositions and methods described herein are envisaged and are within the scope of the invention.

Terms

As used herein, and unless stated otherwise, each of the following terms shall have the definition set forth below.

"Administering to the subject" means the giving of, dispensing of, or application of medicines, drugs, or remedies to a subject to relieve, cure, or reduce the symptoms associated with a condition, e.g., a pathological condition. The route of administration can be, e.g., intramuscular or topical. "Topical administration" of a composition as used herein shall mean application of the composition to the skin of a subject. In an embodiment, topical administration of a composition is application of the composition to the epidermis of a subject.

"Adverse event" or "AE" means any untoward medical occurrence in a patient or clinical investigation subject administered a pharmaceutical product and which does not necessarily have to have a causal relationship with the treatment. An adverse event can therefore be any unfavorable and unintended sign including an abnormal laboratory finding, symptom, or diseases temporally associated with the use of an investigational medicinal product, whether or not considered related to the investigational medicinal product.

"Antibacterial agent" means a bactericidal compound such as silver nitrate solution, mafenide acetate, or silver sulfadiazine, or an antibiotic.

"Biologically active agent" means a substance which has a beneficial effect on living tissue.

"Effective" as in an amount effective to achieve an end means the quantity of a component that is sufficient to yield a desired therapeutic response with a reasonable benefit/risk ratio of side effects. For example, an amount effective to treat pruritus, without causing unreasonable adverse side effects. The specific effective amount will vary with such factors as the particular condition being treated, the physical condition of the patient, the type of mammal being treated, the duration of the treatment, the nature of concurrent therapy (if any), and the specific formulations employed and the structure of the compounds or its derivatives. "Oxygenated perfluorocarbon" is a perfluorocarbon which is carrying oxygen at, for example, saturation or sub-saturation levels.

"Pharmaceutically acceptable carrier" refers to a carrier or excipient that is suitable for use with humans and/or animals without undue adverse side effects (such as toxicity, irritation, and allergic response) commensurate with a reasonable benefit/risk ratio. It can be a pharmaceutically acceptable solvent, suspending agent or vehicle, for delivering the instant compounds to the subject. The carrier may be liquid or solid and is selected with the planned manner of administration in mind.

As used herein, "treating" encompasses, e.g., inducing inhibition, regression, or stasis of, or ameliorating or alleviating a symptom of a condition, e.g., a dermatological condition. "Ameliorating" or "alleviating" a condition or state as used herein shall mean to relieve or lessen the symptoms of that condition or state. "Ameliorate" or "alleviate" with regard to pruritus is to reduce the discomfort or sensation associated with pruritus and/or to reduce tissue damage resulting from or other symptoms associated with pruritus.

As used herein, "Visual Analogue Scale" or "VAS" is a 0-100 mm scale used to score pruritus with 0 mm score indicating no itching; 1-39 mm score indicating mild itching; 40-79 mm score indicating moderate itching and 80-100 mm indicating severe itching.

Perfluoro(tert-butylcyclohexane)

PFCs include perfluoro(tert-butylcyclohexane) ($C_{10}F_{20}$, CAS No. 84808-64-0) which is available, for example, as Oxycyte® or Dermacyte® from Oxygen Biotherapeutics Inc., Morrisville, N.C. Oxycyte® is a perfluorocarbon emulsion oxygen carrier. Dermacyte® is a perfluorocarbon cosmetic gel.

The active ingredient in Oxycyte® and Dermacyte®, perfluoro(tert-butylcyclohexane) ($C_{10}F_{20}$, ~MW-500), also known as F-tert-butylcyclohexane or "FtBu", is a saturated alicyclic PFC. Perfluoro(tert-butylcyclohexane) is a colorless, completely inert, non-water soluble, non-lipophilic molecule, which is twice as dense as water, and boils at 147° C. Oxycyte® and Dermacyte® can be used in the PFC compositions, methods and uses described herein.

In an embodiment, the perfluoro(tert-butylcyclohexane) has the following structure:

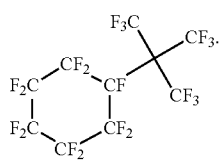

Physical properties of perfluoro(tert-butylcyclohexane) are as follows:

| Molecular Formula | $C_{10}F_{20}$ |
|---|---|
| Molecular Weight (g/mol) | 500.08 |
| Physical State @ Room Temp. | Liquid |
| Density (g/mL) | 1.97 |
| Boiling Point (° C.) | 147 |
| Vapor Pressure (mmHg) @ 25° C. | 3.8 |
| Vapor Pressure (mmHg) @ 37° C. | 4.4 |
| Kinematic Viscosity (cP) | 5.378 |
| Refractive Index @ 20° C. | 1.3098 |
| Calculated Dipole Moment (Debye) | 0.287 |
| Calculated Surface Tension (dyne/cm) | 14.4 |

Perfluoro(tert-butylcyclohexane) can dissolve and release large amounts of gases, including the blood gases oxygen and carbon dioxide. (FtBu can carry about 43 mL of oxygen per 100 mL of PFC, and 196 mL of $CO_2$ per 100 mL of PFC at body temperature) However, Perfluoro(tert-butylcyclohexane) does not exhibit the oxygen binding properties of hemoglobin, but merely acts as a simple gas solvent. As such, no sinusoidal release curve of oxygen is encountered. The transport and release of oxygen and other gases by FtBu is a simple passive process, the quantity of gas dissolved is linearly related to its partial pressure, essentially following Henry's Law.

Being that the PFCS are not lipophilic at room temperature and only slightly lipophilic at body temperature, they can help in the transport of oxygen into and removal of carbon dioxide from, e.g., skin afflicted with pruritus.

Use of Perfluorocarbon for Treatment of Various Dermatological Conditions

The PFC and PFC compositions described herein (e.g., PFC emulsions or PFC gels) can be used for various dermatological conditions including pruritus relief and for providing faster healing of irritated skin. The dermatological conditions which can be treated by the PFC and PFC compositions described herein include, e.g., contact dermatitis, allergic contact dermatitis, histamine induced pruritus, uremic pruritus, photodermatitis, hand dermatitis, eczema, anal pruritus, miliaria rubra, insect bites, xerosis, hemodialysis induced pruritus, aquagenic pruritus, infectious, burn induced pruritus, atopic dermatitis, allergic vulvovaginitis, and allergic and contact dermatitis in animals, e.g., dogs, cats, and horses.

The PFC and PFC compositions can be used for pruritus relief resulting from insect bites, contact dermatitis, atopic dermatitis, eczema, psoriasis etc. Studies have shown that oxygen may inhibit histamine release that is the cause of itch associated with various conditions. It has been disclosed that an oxygen-glucose deprived environment increases histamine release (Shen, 2007). Therefore, the PFC composition can be used, e.g., for relieving pruritus resulting from various underlying conditions.

PFCs have been suggested to have anti-inflammatory properties. Therefore, the PFC compositions can also treat inflammation associated with various skin conditions described herein. The PFC compositions can also reduce redness, swelling and irritation related to, e.g., insect bites, dermatitis, or psoriasis.

By increasing oxygen concentrations, pruritus and general skin irritation can be alleviated. As an additional benefit, the PFC in the gel or emulsion can also anesthetize skin similar, to the way benzocaine does.

Hydrotherapy with perfluorocarbon compositions described herein can be administered as part of the pruritus, psoriasis or dermatitis treatment protocol.

Also, the perfluorocarbon may be administered with aloe vera. Administration of perfluorocarbon in combination with aloe vera allows for delivery of oxygen to the affiliated tissue, as well as coat endothelial cells and decrease edema.

Lastly, perfluorocarbon compositions disclosed herein can be administered along with an antibacterial agent which would decrease infectious complications.

The perfluorocarbon of the methods and compositions of the subject invention may include perfluorocarbon gels or perfluorocarbon-in-water emulsions comprising a continuous aqueous phase and a discontinuous perfluorocarbon phase. The emulsions typically include emulsifiers, buffers, osmotic agents, and electrolytes. The perfluorocarbons can be present in the emulsion from about 5% to 130% w/v. Embodiments include at least about 40%, 45%, 50%, 55%, 60%, 65%, 70%, 75%, 80% and 85% w/v. A 60% w/v F-tert-butylcyclohexane emulsion may be used as the perfluorocarbon emulsion in one embodiment. Embodiments also include an egg yolk phospholipid emulsion buffered in an isotonic medium wherein the perfluorocarbon is present in the emulsion from about 5% to 130% w/v. A 60% w/v F-tert-butylcyclohexane emulsion may be used as the perfluorocarbon emulsion in one embodiment of an egg yolk phospholipid emulsion buffered in an isotonic medium.

The PFC gel can be manufactured, e.g., in accordance with the methods disclosed in U.S. Patent Application Publication No. U.S. 2010-0144861, published Jun. 10, 2010, the entirety of which is hereby incorporated by reference into this application.

The PFC emulsion can be manufactured, e.g., by following the methods disclosed in U.S. Patent Application Publication No. U.S. 2010-0267842, published Oct. 21, 2010, the entirety of which is hereby incorporated by reference into this application.

The compositions of this invention may be administered in forms detailed herein. The use of perfluorocarbon may be a component of a combination therapy or an adjunct therapy. For example, the PFC compositions (emulsion or gel) can be administered with or without another medicament for the treatment of pruritus or the condition underlying the pruritus. The combination therapy can be sequential or simultaneous. The compounds can be administered independently by the same route or by two or more different routes of administration depending on the dosage forms employed.

The dosage of the compounds administered in treatment will vary depending upon factors such as the pharmacodynamic characteristics of a specific therapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect. A dosage unit of the compounds may comprise a single compound or mixtures thereof with other compounds. The compounds can be introduced directly into the targeted tissue, using dosage forms well known to those of ordinary skill in the cosmetic and pharmaceutical arts.

Techniques and compositions for making dosage forms useful in the present invention are described in the following references: Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.). All of the aforementioned publications are incorporated in their entireties by reference herein.

The perfluorocarbon employed in the compositions and methods described herein may be in compositions which may further comprise pharmaceutically acceptable carrier or cosmetic carrier and adjuvant(s) (including pharmaceutical diluents, extenders, excipients, or carriers) suitable for intravenous, intra-arterial, intrathecal, intramuscular or topical administration. This pharmaceutical or cosmetic carrier can be a solid or liquid, and the type of carrier is generally chosen based on the type of administration being used. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Compositions suitable for topical administration are well known in the pharmaceutical and cosmetic arts. These compositions can be adapted to comprise the perfluorocarbon or oxygenated perfluorocarbon. The composition employed in the methods described herein may also comprise a pharmaceutically acceptable additive.

The PFC compositions may contain any of the following non-toxic auxiliary substances:

The multiplicity of configurations may contain additional beneficial biologically active agents which further promote tissue health. The PFC compositions may also contain antibacterial agents which are non-injurious in use, for example, thimerosal, benzalkonium chloride, methyl and propyl paraben, benzyldodecinium bromide, benzyl alcohol, or phenylethanol.

The perfluorocarbon compositions disclosed herein can also comprise excipients such as solubility-altering agents (e.g., ethanol, propylene glycol and sucrose) and polymers (e.g., polycaprylactones and PLGA's) as well as pharmaceutically active compounds.

The PFC compositions may also contain buffering ingredients such as sodium acetate, gluconate buffers, phosphates, bicarbonate, citrate, borate, ACES, BES, BICINE, BIS-Tris, BIS-Tris Propane, HEPES, HEPPS, imidazole, MES, MOPS, PIPES, TAPS, TES, and Tricine.

The PFC compositions may also contain a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, peanut oil, polyalkylene glycols, petroleum based jelly, ethyl cellulose, ethyl oleate, carboxymethyl-cellulose, polyvinylpyrrolidone, isopropyl myristate and other conventionally employed acceptable carriers.

The PFC compositions may also contain non-toxic emulsifying, preserving, wetting agents, bodying agents, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic.

The PFC compositions may also contain surfactants that might be employed include polysorbate surfactants, polyoxyethylene surfactants, phosphonates, saponins and polyethoxylated castor oils, but preferably the polyethoxylated castor oils. These surfactants are commercially available. The polyethoxylated castor oils are sold, for example, by BASF under the trademark Cremaphor.

The PFC compositions may also contain wetting agents commonly used in ophthalmic solutions such as carboxymethylcellulose, hydroxypropyl methylcellulose, glycerin, mannitol, polyvinyl alcohol or hydroxyethylcellulose and the diluting agent may be water, distilled water, sterile water, or artificial tears, wherein the wetting agent is present in an amount of about 0.001% to about 10%.

The formulation of this invention may be varied to include acids and bases to adjust the pH; tonicity imparting agents such as sorbitol, glycerin and dextrose; other viscosity imparting agents such as sodium carboxymethylcellulose, microcrystalline cellulose, polyvinylpyrrolidone, polyvinyl alcohol and other gums; suitable absorption enhancers, such as surfactants, bile acids; stabilizing agents such as antioxidants, like bisulfites and ascorbates; metal chelating agents, such as sodium edetate; and drug solubility enhancers, such as polyethylene glycols. These additional ingredients help make commercial solutions with adequate stability so that they need not be compounded on demand.

Other materials as well as processing techniques and the like are set forth in Part 8 of Remington's Pharmaceutical Sciences, 17th edition, 1985, Mack Publishing Company, Easton, Pa., and International Programme on Chemical Safety (IPCS), which is incorporated herein by reference.

It is understood that where a parameter range is provided, all integers within that range, and tenths thereof, are also provided by the invention. For example, "1-6 hours" includes 1.0 hours, 1.1 hours, 1.2 hours, 1.3 hours, 1.4 hours etc. up to 6.0 hours.

All combinations and sub-combinations of the various elements of the methods described herein are envisaged and are within the scope of the invention.

This invention will be better understood by reference to the Experimental Details which follow, but those skilled in the art will readily appreciate that the specific experiments detailed are only illustrative of the invention as described more fully in the claims which follow thereafter.

Experimental Details

EXAMPLE 1

A Single Blind Study Assessing the Efficacy of a FtBu Gel in Relieving Pruritus Secondary to a Histamine Prick Test Materials and Method:
The standard histamine prick test was utilized to create a localized area of acute allergic response (classic wheal and flare reaction). The method involved placing a small drop of histamine on each subject's forearm and wrist. To initiate the allergic reaction, a sharp needle is then used to "prick" the skin just under the histamine. Fourteen (14) subjects each had two standardized histamine prick tests. An FtBu gel (Dermacyte®, from Oxygen Biotherapeutics, Inc., Morrisville, N.C.) was then applied in blinded fashion at the one site 10 minutes after the reaction was initiated and after 20 minutes for the other. Extent of pruritus was then assessed by asking each subject to judge the severity of the itching at the site. In addition, the Investigator scored the edema and erythema at each site.

Histamine Prick Test (Darsow, 2000):
1. Causes an immediate wheal (edema) and flare (erythema) reaction that is graded 0-4.
2. Subject is then treated with either a moisturizing cream or FtBu.

Primary End Points: Subject perception of itching at each prick test sites.

Secondary End Point: Decrease in size of edema and erythema secondary to prick test.

Exploratory End Point: Onset of anti-pruritic effect compared to potent steroid cream (Elocon)

Results:
1. Thirteen out of the fourteen subjects developed pruritus secondary to the histamine test.
2. Twelve out of the thirteen subjects who developed pruritus reported less itching with the application of Dermacyte® than at the untreated reaction at 10 and 20 minutes
3. It was the investigator's impression that the wheal and flare (edema and erythema) appeared smaller after the application of Dermacyte®.
4. It was the investigator's impression that Dermacyte® worked faster than a potent steroid cream, Elocon.

Discussion:
This study demonstrated the efficacy of Dermacyte® in decreasing histamine-induced pruritus. Dermacyte® decreased the size of the histamine induced edema and erythema. It also had a faster onset of action than some topical steroids in reducing itch.

EXAMPLE 2

Clinical Trial—Assessment of Dermacyte® Cosmetic Gel in Relieving Histamine-Induced Pruritus and Wheal and Flare Reaction A prospective, randomized, double blind, placebo-controlled study is conducted to assess the efficacy of Dermacyte® cosmetic gel in reducing acute histamine-induced itch and the accompanying wheal (edema) and flare (erythema) reaction. The impact of the topical product on the two phenomena is monitored over time and the effects are compared to those of a placebo.

Background
The sensation of itch is the most prevalent and uncomfortable symptom of many types of allergic and inflammatory skin diseases (Behrendt et al, 2001; Charlesworth and Beltrani, 2002). During the cutaneous allergic and inflammatory reactions underlying these diseases, histamine is released following sensitization and degranulation of the mast cells (Krishnamoorthy et al, 2011). The subsequent itching invariably leads to scratching that can cause mechanical trauma to the skin, further damaging the epidermal barrier and its function, and, potentially, facilitating the introduction of microbes that often leads to secondary infections. This itching (or pruritus) is a major factor in the decreased quality of life experienced by many sufferers of allergic skin conditions.

In studies examining the anti-pruritic action of a compound, a histamine skin prick test is typically used for initiating the itch (as well as wheal and flare) response. In a histamine skin prick test, 1% histamine dihydrochloride is applied as a single drop in aqueous solution on the skin followed by superficial puncture of the skin by a special lancet (Ring, 2005). The resulting deposition of histamine solution at the dermal—epidermal junction, produces a strong itch reaction (Shelley and Arthur, 1957; Darsow et al, 1996). Stabilization of mast cells to prevent degranulation and release of histamine and/or neutralization of the released histamine using anti-histamines (Hanifin, 1984; Gisela et al., 1989) and use of topical corticosteroids as anti-inflammatory agents play an important role in the management of pruritus-related allergic diseases.

Pruritus is often associated with sunburns, allergic reactions, eczema, psoriasis, fungal infections, insect bites and stings, contact dermatitis, and urticaria and adversely affects the quality of life in these subjects. Standard treatment involves oral treatment with anti-histamines and/or topical corticosteroids which may cause significant side effects such as hyperglycemia, fluid and electrolyte imbalance, increase in appetite, sedation, thinning of the skin, stria, and all with long term use or the use of potent steroids, systemic steroids effects (hypertension, hyperglycemia, etc) while topical antihistamine can cause sedation, or can be sensitizing.

Therefore there is an unfulfilled and immediate need for alternative treatment options that have reduced side effect profile.

Dermacyte® is a proprietary topical cosmetic gel which contains perfluoro(tert-butylcyclohexane), a third-generation, proprietary PFC, therapeutic oxygen carrier product formulated for topical delivery. It was developed by Oxygen Biotherapeutics, Inc. (Morrisville, N.C.) to enhance oxygen delivery to the skin. Dermacyte® is currently marketed in the United States, Switzerland, and Mexico for enhancing skin health and as a treatment for fine lines and wrinkles. While the mechanism is unknown, it is thought that the unique oxygen delivery action of Dermacyte® may contribute to the anti-pruritic property of the cosmetic.

Dermacyte® has been evaluated in rabbits for irritation and delayed-type hypersensitivity, and in guinea pigs for delayed thermal contact sensitization. Dermacyte® was found to elicit no irritation, negligible hypersensitivity response, and produce no evidence of causing delayed dermal contact sensitization. Dermacyte® has also been found to produce no abnormal cell morphology or cell lysis when tested for cytotoxicity on L-929 mouse fibroblast cells. Studies in humans have demonstrated that Dermacyte® is a non-irritant and non-sensitizer, and found to be safe without any adverse reactions.

Study Title

A Prospective, Randomized, Double blind, Placebo-controlled Study to Determine the Efficacy of Dermacyte® Cosmetic Gel in Relieving Histamine-induced Pruritus and Wheal and Flare Reaction.

Study Design

This study is a single-center, double-blind, placebo controlled comparative study in which 30 healthy subjects undergo a standard histamine skin prick test on each arm, for a total of two test sites per subject.

The total duration of the study is 3 months and consists of two months for subject enrollment and treatment, and one month for site close out activities. For the individual subject, duration of the study is a single visit which lasts an estimated 2-3 hours, and includes all screening, and treatment procedures.

Treatment Arms

Eligible subjects are randomized into one of the following treatment groups:
1. Dermacyte® cosmetic gel.
2. Placebo.

Test Procedure

In this study, each subject serves as his/her own internal control. Since there is a substantial reduction of within-subject variability compared to the between-subject variability, this design is more efficient than a parallel group design. Therefore, for each subject Dermacyte® is applied to the test area on one arm with placebo applied to the test site on the other arm.

Each subject receives on the volar aspect of each arm a single histamine prick test. The preferred areas of the arms are the volar surfaces from the axilla to 2.5 or 5 cm above the wrist, skipping the anti-cubital space. The area is sterilized with spirit without rubbing. A drop of histamine or normal saline as negative control is applied on the skin at least 2.5 cm apart. The skin is pricked through the drop with a sterile lance or 21 gauge needle. Areas that are very hairy are avoided.

Immediately following (30-60 seconds) each histamine prick test on each arm, a small amount of Dermacyte® or placebo forming a thin layer is applied evenly at and around the site of the histamine skin prick. It is applied only once during the treatment cycle of this study. The level of itch and extent of wheal and flare reaction is then measured at 5, 15, and 30 minutes using the VAS and a ruler, respectively. Effect of product is followed up for up to 30 minutes post application. A stopwatch is used to record time since application. The basic design for the study is illustrated in FIG. 1.

Visual Analogue Scale

The VAS score is recorded three times at 5, 15 and 30 minutes after application of Dermacyte® or placebo.

Visual Analog Scale (VAS) has long been used to assess various sensations and has been found to be more reproducible than verbal descriptor scales (Rosier et al., 2002). A VAS score of 0-100 mm is used to assess different grading of itch: Score of 0 mm: no itch; Score of 1-39 mm: mild; Score of 40-79 mm: moderate; and Score of 80-100 mm: severe unbearable itch.

Measurement of Wheal & Flare

The wheal & flare is assessed by measuring the diameter of the wheal & flare using a standard ruler (mm). The longest diameter will be measured in cases where the wheal and flare reaction on the skin is irregular in shape (Konstantinou, 2010) (See FIG. 1).

Adverse Events (AEs)

AEs are recorded from the time the informed consent is signed through the end of each subject's participation in the study. AEs are evaluated for potential relationship to Dermacyte® as well as the seriousness and expectedness of each event. Serious AEs (SAEs) and Suspected Unexpected Serious Adverse Reactions (SUSARs) are reported to authorities and followed-up according to local requirements.

Statistical Strategy

This study is a pilot study to determine the efficacy of Dermacyte® cosmetic gel in relieving histamine-induced pruritus as well as wheal and flare reaction. The sample size of 30 healthy volunteers was based on clinical considerations.

The descriptive statistics for continuous variables is presented as the number (N) of non-missing observations, mean, standard deviation (sd), median, minimum, and maximum. For categorical data, descriptive statistics is presented as the number of exposed subjects, and number (N) of observations with percentage in various categories of the endpoint. The percentage is based on the exposed subjects. The treatment groups are compared for average reduction in VAS score (for itching) and wheal & flare diameter from 5 min, 15 min, and 30 min using paired t-test at 5% level of significance.

All statistical tests are two-sided and P-value<0.05 is considered statistically significant.

Inclusion/Exclusion Criteria

Inclusion Criteria

1. Healthy male or female subjects aged 18-65 years (inclusive).
2. Female subjects of childbearing potential must have negative pregnancy test at screening.
3. Signed informed consent form.

Exclusion Criteria

1. Subjects with a history of skin irritation or infection in the past 6 months in the intended areas of the histamine skin prick test.
2. Subjects with any contraindications involving performance of a histamine skin prick test.
3. Subjects with a medical history of asthma, eczema or other atopic allergy.
4. Subjects with active skin disease.
5. Pregnant or nursing subjects.
6. Use of any investigational drug or therapy within 6 months prior to screening.
7. Use of any creams, lotions, or other ointments on either arm within 72 hours prior to enrollment.
8. Subjects who have taken any of the following medications:
    Any anti-inflammatory drug (e.g., Ibuprofen) within the last week.
    Any H1 histamine antagonist or other medications with antihistaminic properties (e.g., tricyclic antidepressants) within the last 2 weeks.
    Any topical or systemic steroid product within the 2 months.
9. Subjects with any clinically significant medical conditions which, as determined by the Investigator, would compromise interpretation of the study results.
10. Any other factor, which may, in the opinion of the Investigator, compromise subject participation or risk subject safety in this study.

Prohibited Medications 1. creams, lotions, or other ointments
2. Any anti-inflammatory drug (e.g., Ibuprofen)
3. H1 histamine antagonists or other medications with antihistaminic properties (eg. tricyclic antidepressants)
4. Any topical or systemic steroid product Outcome Measures The first efficacy endpoint of the study is measurement of the reduction of itch following the histamine skin prick test. The efficacy of Dermacyte® in reducing acute histamine-induced itch is assessed as reported by each subject using a standard Visual Analogue Scale (VAS).

The second efficacy endpoint of the study is measurement of the reduction of the wheal & flare reaction following the histamine skin prick test. The ability of Dermacyte® to reduce the wheal and flare reaction is measured by the Principal Investigator using a ruler. Measurements for itch and the wheal and flare are made at 5, 15, and 30 minutes after application of either the Dermacyte® cosmetic gel or placebo. Following this method, the duration of action can also be studied.

AEs are summarized and tabulated by MedDRA Version 14.0 body system and preferred term, indicating number and percentage of subjects and number of events. Concomitant medications, concurrent illnesses and medical history, are listed by subject.

Results/Discussion

This study shows that Dermacyte® can effectively treat pruritus and reduce the sensation of pruritus in a subject. Application of Dermacyte® effectively reduces subject-perceived itching, as measured by VAS score, as compared to the application of a placebo. In addition, application of Dermacyte® effectively reduces wheal and flare reaction of a subject, as compared to the application of a placebo. Application of Dermacyte® also effectively reduces the duration of subject-perceived itching and/or wheal and flare reaction of a subject, as compared to the application of a placebo.

The results of this study indicates that the application of Dermacyte® to the skin affected with pruritus effectively reduces itch, as measured by subject-reported VAS score, as compared to the application of a placebo. Application of Dermacyte® to the skin also effectively reduces the wheal & flare reaction of the affected area of the skin, at 5, 15, and 30 minutes after application of the Dermacyte®. Application of Dermacyte® to the skin also effectively reduces the duration of the wheal & flare reaction. Finally, application of Dermacyte® to the skin is safe and well tolerated by the subject.

Therefore, Dermacyte® provides a safe and rapid solution to itch relief by enhancing oxygen delivery to the upper layers of the skin.

EXAMPLE 3

Allergic Pruritus

Four individuals have reported relief of itching secondary to insect bites. It was reported that relief occurred almost immediately and lasted approximately 3 hours. One individual stated that it was as effective as mometasone.

Two case reports have reported that contact dermatitis was resolved rapidly with the administration of Dermacyte®.

One patient being treated for atopic dermatitis reported quick improvement in itching lasting 3-4 hours. It was also reported that erythematous lesions improved.

EXAMPLE 4

Psoriasis

A perfluorocarbon composition as described herein is administered to a subject afflicted with psoriasis.

The administration the PFC composition is effective to alleviate a symptom of psoriasis, relieve pruritus associated with the psoriasis, improve the appearance of the skin where the composition is applied, reduce subject's perceived itching and increase anti-inflammatory activity on the skin where the composition is applied.

The administration of the PFC composition is also effective to reduce edema, erythema and erythematous lesions.

EXAMPLE 5

Pruritus

A perfluorocarbon composition as described herein is administered to a subject afflicted with pruritus.

The administration the PFC composition is effective to treat the pruritus, reduce subject's perceived itching and increase anti-inflammatory activity on the skin where the composition is applied.

The administration of the PFC composition is also effective to reduce edema, erythema and erythematous lesions.

EXAMPLE 6

Pruritus Resulting From Xerosis

A perfluorocarbon composition as described herein is administered to a subject afflicted with xerosis.

The administration the PFC composition is effective to treat the pruritus resulting from xerosis, reduce subject's perceived itching and increase anti-inflammatory activity on the skin where the composition is applied.

The administration of the PFC composition is also effective to reduce edema, erythema and erythematous lesions.

EXAMPLE 7

Pruritus Resulting From Atopic Dermatitis (AD)

A perfluorocarbon composition as described herein is administered to a subject afflicted with atopic dermatitis.

The administration the PFC composition is effective to treat the pruritus resulting from the dermatitis, decrease release of histamine, decrease acute exacerbations, reduce subject's perceived itching and increase anti-inflammatory activity on the skin where the composition is applied.

The administration of the PFC composition is also effective to reduce edema, erythema and erythematous lesions.

EXAMPLE 8

Pruritus Resulting From Contact Dermatitis

A perfluorocarbon composition as described herein is administered to a subject afflicted with contact dermatitis.

The administration the PFC composition is effective to treat the pruritus resulting from the dermatitis, decrease release of histamine, decrease acute exacerbations, reduce subject's perceived itching and increase anti-inflammatory activity on the skin where the composition is applied.

The administration of the PFC composition is also effective to reduce edema, erythema and erythematous lesions.

EXAMPLE 9

Pruritus Induced By Histamine

A perfluorocarbon composition as described herein is administered to a subject afflicted with histamine-induced pruritus.

The administration the PFC composition is effective to treat the histamine-induced pruritus, decrease release of histamine, decrease acute exacerbations, reduce subject's perceived itching and increase anti-inflammatory activity on the skin where the composition is applied.

The administration of the PFC composition is also effective to reduce edema, erythema and erythematous lesions.

EXAMPLE 10

Dermatological Allergic Response

A perfluorocarbon composition as described herein is administered to a subject afflicted with a dermatological allergic response.

The administration the PFC composition is effective to alleviate a symptom of the dermatological allergic response, treat pruritus resulting from the dermatological allergic response, reduce subject's perceived itching and increase anti-inflammatory activity on the skin where the composition is applied. The administration of the PFC composition is also effective to reduce edema or erythema associated with the allergic response.

EXAMPLE 11

Inflammatory Skin Condition

A perfluorocarbon composition as described herein is administered to a subject afflicted with an inflammatory skin condition.

The administration the PFC composition is effective to alleviate a symptom of the inflammatory skin condition, treat pruritus resulting from the inflammatory skin condition, reduce subject's perceived itching and increase anti-inflammatory activity on the skin where the composition is applied. The administration of the PFC composition is also effective to reduce edema or erythema associated with the inflammatory skin condition.

EXAMPLE 12

Edema

A perfluorocarbon composition as described herein is administered to the skin of a subject afflicted with edema.

The administration the PFC composition is effective reduce the edema.

EXAMPLE 13

Erythema

A perfluorocarbon composition as described herein is administered to the skin of a subject afflicted with erythema.

The administration the PFC composition is effective reduce the erythema.

References

1. "Dermatitis" *The Merck Manual,* 17th ed. Mark H. Beers, MD, Robert Berkow, MD, eds. Whitehouse Station, N.J.: Merck Research Labs, 1999, pp. 786-789.
2. "Pruritus" *The Merck Manual,* 17th ed. Mark H. Beers, MD, Robert Berkow, MD, eds, Whitehouse Station, N.J.: Merck Research Labs, 1999, pp. 782.
3. "Psoriasis" *The Merck Manual,* 17th ed. Mark H. Beers, MD, Robert Berkow, MD, eds. Whitehouse Station, N.J.: Merck Research Labs, 1999, pp. B16-818.
4. Behrendt at al. (2001). "Allergotoxicology—A research concept to study the role of environmental pollutants in allergy." *ACI Int* 13:122-8 Butler G. (2009) "Therapeutic Effect of Hyperbaric Oxygen in Psoriasis Vulgaris: Two Case Reports and Review of the Literature." *J. Med Case Rep.* 3:7023.
5. Charlesworth and Beltrani (2002). "Pruritic dermatoses: overview of etiology and therapy." *Am J. Med.* 113:25 S-33S.
6. Darsow at al. (1996) "Correlations between histamine-induced wheal, flare and itch." *Arch Dermatol Res.* 288: 436-41.
7. Darsow (2000) "Processing of Histamine-Induced Itch in the Human Cerebral Cortex: A Correlation Analysis with Dermal Reactions." *Journal of Investigative Dermatology,* 115:1029-1033.
8. Davis S. (2007) "Topical Oxygen Emulsion, A Novel Wound Therapy." *Arch Dermatology* 143:1252-1256.
9. Gisela at al. (1989). "Skin reactions and itching sensation induced by epicutaneous Histamine application in atopic dermatitis and controls." *J. Invest. Dermatol.* 93: 492-496.
10. Hanifin J M (1984). "Basic and Clinical aspects of atopic dermatitis." *Ann. Allergy.* 52: 396-395.

11. Konstantinou et al. (2010) "The longest wheal diameter is the optimal measurement for the evaluation of skin prick tests" *Int Arch Allergy Immunol.* 151(4):343-5.
12. Krishnamoorthy et al. (2011) "Effect of topical application of 07 in reducing histamine induced skin reactions: A preliminary study." *Journ of Med Plants Res.* Vol, 5(10), pp. 2104-2106.
13. Lehmler H. (2008) "Anti-inflammatory Effects of Perfluorocarbon Compounds." *Exp Rev Res Med.* 2:273-289.
14. McDongh P. (2001) "Perflubron Emulsion Reduces Inflammation during Extracorporeal Circulation." *J. Surg. Res.* 99:7-16.
15. Ring J (ed). (2005) "Allergy in Practice." Berlin, Heidelberg, New York: Springer, 246 pp.
16. Rosier et al. (2002) "Reproducibility Of Pain Measurement and Pain Perception" *Pain.* 98(1-2):205-216.
17. Sarafidis H. (2008) "Perfluorochemical Augmented Delivery Attenuates Inflammation in the Immature Lung." *J. NeoNat Perna Med.* 2008:1.
18. Shelley and Arthur (1957) "The neurohistology and neurophysiology of the itch sensation in man." *Arch Dermatol.* 76:296-323.
19. Shen, Yao, et al. (2007) "Carnosine attenuates mast cell degranulation and histamine release induced by oxygen-glucose deprivation" *Cell Biochemistry and Function.* 26(3):334-338.

What is claimed is:

1. A method of treating pruritus comprising administering to the skin of a subject afflicted with pruritus an amount of a perfluorocarbon effective to treat the pruritus.

2. The method of claim 1, wherein the pruritus is induced by histamine, a burn, an infection or hemodialysis.

3. The method of claim 1, wherein the pruritus is a symptom of an inflammatory skin condition, xerosis, an insect bite, a dermatological allergic response, allergic dermatitis, allergic contact dermatitis, photodermatitis, hand dermatitis, miliaria rubra, eczema, atopic dermatitis or contact dermatitis.

4. The method of claim 3, wherein the inflammatory skin condition is psoriasis or allergic vulvovaginitis.

5. The method of claim 1, wherein the pruritus is anal pruritus, uremic pruritus or aquagenic pruritus.

6. A method of alleviating a symptom of psoriasis comprising administering to the skin of a subject afflicted with psoriasis an amount of a perfluorocarbon effective to alleviate the symptom of psoriasis.

7. The method of claim 6, wherein the symptom is pruritus.

8. The method of claim 1, wherein the molecular formula of the perfluorocarbon consists 9-12 carbon atoms.

9. The method of claim 1, wherein the perfluorocarbon is perfluoro(tert-butylcyclohexane) perfluoro-n-butylcyclohexane, perfluorodecalin, trimethyl perfluorodecalin, perfluoroisopropyldecalin, perfluoro-tripropylamine, perfluorotributylamine, perfluoro-methylcyclohexylpiperidine, perfluoro-octylbromide, perfluoro-decylbromide, perfluoro-dichlorooctane, perfluorohexane, dodecafluoropentane, or a mixture thereof.

10. The method of claim 9, wherein the perfluorocarbon is perfluoro(tert-butylcyclohexane) or perfluoro-n-butylcyclohexane.

11. The method of claim 1, wherein the perfluorocarbon is in a perfluorocarbon gel or emulsion.

12. The method of claim 1, wherein the subject is afflicted with edema, erythema or erythematous lesion.

13. The method of claim 1, wherein the administration of the perfluorocarbon reduces subject-perceived itching.

14. The method of claim 1, wherein the administration of the perfluorocarbon relieves the subject's pruritus for 3 hours or more.

15. The method of claim 1, wherein the administration of the perfluorocarbon relieves the subject's pruritus within 1 minute of the administration.

16. The method of claim 1, wherein the subject is human.

17. The method of claim 6, wherein the perfluorocarbon is perfluoro(tert-butylcyclohexane) or perfluoro-n-butylcyclohexane.

18. The method of claim 6, wherein the perfluorocarbon is in a perfluorocarbon gel or emulsion.

19. The method of claim 7, wherein the administration of the perfluorocarbon relieves the subject's pruritus for 3 hours or more.

20. The method of claim 7, wherein the administration of the perfluorocarbon relieves the subject's pruritus within 1 minute of the administration.

* * * * *